United States Patent
Georgii et al.

(10) Patent No.: US 10,292,683 B2
(45) Date of Patent: May 21, 2019

(54) METHOD AND DEVICE FOR RECORDING AN ULTRASOUND IMAGE OF A DEFORMED OBJECT, IN PARTICULAR THE HUMAN BREAST

(71) Applicant: SIEMENS AKTIENGESELLSCHAFT, Munich (DE)

(72) Inventors: Joachim Georgii, Bremen (DE); Marcus Radicke, Veitsbronn (DE); Fabian Zoehrer, Bremen (DE)

(73) Assignee: Siemens Aktiengesellschaft, Munich (DE)

( * ) Notice: Subject to any disclaimer, the term of this patent is extended or adjusted under 35 U.S.C. 154(b) by 700 days.

(21) Appl. No.: 14/902,884

(22) PCT Filed: Jul. 2, 2014

(86) PCT No.: PCT/EP2014/064072
§ 371 (c)(1),
(2) Date: Jan. 5, 2016

(87) PCT Pub. No.: WO2015/000962
PCT Pub. Date: Jan. 8, 2015

(65) Prior Publication Data
US 2016/0151050 A1      Jun. 2, 2016

(30) Foreign Application Priority Data

Jul. 5, 2013   (DE) .................. 10 2013 213 215

(51) Int. Cl.
*A61B 8/08*      (2006.01)
*A61B 5/00*      (2006.01)
(Continued)

(52) U.S. Cl.
CPC .......... *A61B 8/5215* (2013.01); *A61B 5/0035* (2013.01); *A61B 5/055* (2013.01);
(Continued)

(58) Field of Classification Search
CPC ... A61B 8/5215; A61B 5/1114; A61B 8/4254; A61B 8/0825; A61B 8/463;
(Continued)

(56) References Cited

U.S. PATENT DOCUMENTS

| 6,768,496 B2* | 7/2004 | Bieger ................... A61B 5/065 345/630 |
| 2004/0138559 A1* | 7/2004 | Cheng .................. A61B 8/0825 600/437 |

(Continued)

FOREIGN PATENT DOCUMENTS

| DE | 10015826 A1 | 10/2001 |
| DE | 102012213923 A1 | 2/2014 |
| WO | 2013101562 A2 | 7/2013 |

OTHER PUBLICATIONS

Lago, M.A., et al., "Breast prone-to-supine deformation and registration using a Time-of-Flight camera," Biomedical Robotics and Biomechatronics (BioRob), 4th IEEE RAS & EMBS International Conference, pp. 1161-1163, Jun. 24-27, 2012.

(Continued)

*Primary Examiner* — Sanjay Cattungal
(74) *Attorney, Agent, or Firm* — Laurence Greenberg; Werner Stemer; Ralph Locher

(57) ABSTRACT

A relationship is established between points or regions in images of objects deformed in different ways, for example images of the human chest in a mammography and 3D ultrasound process. While a plurality of recording parameters which can be used for such an automatic image registration are often known in X-ray and other imaging (Continued)

methods, precise recording parameters, in particular for the position of the chest, are usually not available in ultrasound processes. The object is to additionally detect the position, in particular the tilt, of the chest and the ultrasound transducer in a chest ultrasound. A linking of multiple ultrasound recordings to one another or a comparably more precise automatic image registration using other modalities can then be carried out using the position of the ultrasound transducer relative to the chest. The position is detected in a manner that is specific to the case.

12 Claims, 3 Drawing Sheets

(51) Int. Cl.
    *A61B 8/00*         (2006.01)
    *A61B 5/055*       (2006.01)
    *A61B 5/11*         (2006.01)
    *G06T 7/33*         (2017.01)

(52) U.S. Cl.
    CPC .......... *A61B 5/1114* (2013.01); *A61B 5/4312* (2013.01); *A61B 5/721* (2013.01); *A61B 8/0825* (2013.01); *A61B 8/4254* (2013.01); *A61B 8/463* (2013.01); *G06T 7/344* (2017.01); *G06T 2207/10116* (2013.01); *G06T 2207/10132* (2013.01); *G06T 2207/30068* (2013.01)

(58) Field of Classification Search
    CPC ..... A61B 5/0035; A61B 5/055; A61B 5/4312; A61B 5/721; G06T 7/344; G06T 2207/10116; G06T 2207/10132; G06T 2207/30068
    USPC .................................................. 600/437–469
    See application file for complete search history.

(56) References Cited

U.S. PATENT DOCUMENTS

| | | | |
|---|---|---|---|
| 2007/0038085 A1* | 2/2007 | Zhang | A61B 6/463 600/437 |
| 2011/0190629 A1* | 8/2011 | Guenther | A61B 8/08 600/437 |
| 2012/0015037 A1 | 1/2012 | Hsieh et al. | |

OTHER PUBLICATIONS

Carter T. et al, "MR Navigated Breast Surgery: Method and Initial Clinical Experience"; Medical Image Computing, and Computer-Assisted Intervention—MICCAI 2008, pp. 356-363; Springer Verlag, Berlin Heidelberg; ISBN: 978-3-540-85989-5; XP019105179.

"ABVS Ultraschall Brust-Scan in 3D"; Youtube: http://ww.youtube.com./watch?v=18PJOUNMjtQ; XP054975525; 2013.

Rohling et al:"Automatic registration of 3-D ultrasound images"; Ultrasound in medicine and biology, 1998, pp. 841-854; vol. 24; No. 6; Elsevier; ISSN: 0301-5629; DOI: 10.1016/S0301-5629(97)00210-X; XP004295313.

Chung J.H. et al; "Modelling Mammographic Compression of the Breast", Medical Computing and Computer-Assisted Intervention—MICCAI 2008, pp. 758-765; Springer Verlag Berlin, Heidelberg; ISBN: 978-3-540-85989-5; XP019105232.

Wei-Wei J., et al:"An automated 3D annotation method for breast ultrasound imaging"; the effect of applied compressive loading on Tissue-Engineered cartilage constructs cultured with TGF-BETA3, IEEE; 2012, pp. 488-491; ISSN: 1557-170X; DOI:10.1109/EMBC.2012.6345974; XP032462962.

* cited by examiner

METHOD AND DEVICE FOR RECORDING AN ULTRASOUND IMAGE OF A DEFORMED OBJECT, IN PARTICULAR THE HUMAN BREAST

BACKGROUND OF THE INVENTION

Field of the Invention

The invention relates to a method and a device for recording an ultrasound image of a deformed object, in particular the human breast. Moreover, the invention relates to a method and a device for determining selected points and/or regions in medical recordings of an object deformed in various ways, in particular the human breast.

Early detection of breast cancer is a huge challenge for all currently existing medical imaging methods. There is large agreement in the whole medical research sector that a diagnosis with high sensitivity and specificity at the same time can only be obtained by the skillful combination of various imaging methods. Therefore, an object consists of bringing together various measurement techniques in order thus to be able to superpose the obtained images as exactly as possible or link said images to one another.

Until now, software-assisted image superposition has failed as a result of the breast experiencing different deformations in the various recordings. By way of example, the breast is clamped between two plates in mammography and therefore typically compressed in the craniocaudal and/or mediolateral/mediolateral oblique direction. By contrast, in an automated breast ultrasound, the breast is pressed against the rib cage by the ultrasound head. It is therefore conventional practice for the images obtained by the individual modalities only to be superposed "in the head" of the radiologist. In general, only very experienced radiologists succeed therein with a sufficiently good result.

BRIEF SUMMARY OF THE INVENTION

It is an object of the present invention to simplify the evaluation of medical image data. This object is achieved by methods as claimed and by a device as claimed. Advantageous embodiments of the invention are specified in the dependent claims. The advantages and embodiments explained below in conjunction with the method also apply correspondingly to the devices according to the invention, and vice versa.

Below, exemplary terms are sometimes used instead of superordinate terms, without this being intended to be understood in a restrictive manner. Thus, the human breast is sometimes referred to as an example for an object to be recorded and an x-ray recording is referred to as an example for recording that is different from an ultrasound recording.

The invention proceeds from the recognition that it is important to know the respective recording locations at least approximately for software-assisted superposition or registration of ultrasound and x-ray images (2D/3D). While x-ray recordings are implemented using similar recording locations in each case and the corresponding geometric parameters of the recording, such as e.g. compression direction, compression force and plate distance, are stored in the DICOM text of the image, the position, in particular the tilt of the patient can however vary strongly in ultrasound recordings in a manner dependent on the patient and/or the examiner carrying out the recording. Therefore, a core concept of the invention lies in recording this examiner-specific and patient-specific position and tilt of the breast during ultrasound recordings and using these for an automated image registration with recordings from other imaging methods. Here, it is not the object of the invention to carry out a real superposition within the meaning of image fusion. Rather, there should be an identification in a different representation of a point or region that was located in one representation. To this end, a correlation is established between coordinates in models of the differently deformed object, cf. patent application DE 10 2012 213 923 ("Apparatus and method for position correlation in medical recordings"). This is implemented by virtue of a relationship being established between the coordinates of a selected point or region in a first deformation model and the corresponding coordinates in a second deformation model using the non-deformed initial model of the object. Such a coordinate correlation means that the coordinates of the first deformation model, which correspond to the selected point or region, are correlated with the corresponding coordinates in the second deformation model. Expressed differently, the selected point or region from the first deformation model is mapped into the second deformation model. Here, the first deformation model represents the deformed object during the first recording, with the recording data record from the first recording being linked to the first deformation model, and the second deformation model represents the deformed object during the second recording, with the recording data record of the second recording being linked to the second deformation model. Therefore, selecting a specific point or region in one of the deformation models is always implemented on the basis of the image information of the corresponding recording that is mapped there. Therefore, with the aid of the invention, it is possible to display the point or region selected in one recording, for example in an x-ray recording, in the other recording, for example an ultrasound recording. Expressed differently, the coordinates which correspond to the point or region in one of the recordings can be displayed in the other recording. As a result of the proposed acquisition of location and/or orientation of the breast, a comparatively exact, automated and software-assisted assignment of individual points or regions in recordings of differently deformed objects is made possible for the first time, with the invention being applicable both to an automated breast volume ultrasound (ABVS) and a manual breast ultrasound. Instead of a superposition of the images "in the head" of the radiologist, an accurate software-assisted determination of mutually corresponding images or image portions is possible.

The information about the position of the object and/or the position of the ultrasound recording instrument during the recording, which are required for linking the data, preferably comprises information about the location and/or orientation of the object, in particular information about the tilt of the object relative to an initial location. Moreover, it may be advantageous for an even more precise and/or quicker image registration if the information about the position of the object and/or the ultrasound recording instrument during the recording comprises information about the location and/or orientation of the ultrasound recording instrument, in particular information about a tilt of the ultrasound recording instrument relative to an initial location, and/or information about a movement of the ultrasound recording instrument during the recording. Information about a movement of the object is usually not required since the patient does not move during the recording. With the aid of this information it is possible to implement the identification of the corresponding points or regions in a patient-specific and examiner-specific manner, even in the case of ultrasound recordings. Here, the case-specific acquisition of the rib cage alignment of the patient and the position of the ultrasound head, in particular, leads to an increase in the accuracy during the automated software registration of ultrasound and x-ray images of the breast.

What is particularly advantageous is that no complicated and expensive measurement apparatuses or sensors are required for acquiring information about the position of the object and/or the ultrasound recording instrument during the recording since a few items of position information, in particular in relation to the tilt of the rib cage, already suffice for a significantly improved registration. The corresponding information can instead be obtained with the aid of simple, cost-effective sensors, in particular by using gyro sensors.

A further core concept of the invention lies in recording the examiner-specific and patient-specific position and tilt of the breast during ultrasound recordings and using these for an automatic image registration with other ultrasound recordings of this object. A simplified evaluation of medical image data is therefore already possible with the aid of the present invention by virtue of it being possible to relate a plurality of ultrasound recordings of an object to one another with the aid of the position information established during the ultrasound recordings. By way of example, a plurality of individual recordings can be automatically superposed or aligned in relation to one another on the basis of the position information such that an overall volume describing the object more comprehensively emerges. In other words, the present invention is not restricted to bringing together data which were required by the application of different modalities. The invention is also applicable to ultrasound recordings only. If ultrasound recordings should moreover also be linked with recordings from other imaging methods, it is moreover particularly advantageous if these ultrasound recordings were previously linked to one another in a manner according to the invention.

In conclusion, the invention therefore firstly describes the bringing together or registration of ultrasound recordings and, secondly, the automated registration of ultrasound recordings with recordings from other imaging methods, such as 2D or 3D x-ray and/or magnetic resonance imaging methods, by using additional orientation information of the ultrasound volume in relation to the object.

The device according to the invention is embodied to carry out the above-described method. Preferably the device comprises a data processing unit, which is embodied to carry out all steps corresponding to the method described here, which steps are associated with the processing of data. The data processing unit preferably has a number of functional modules, wherein each functional module is embodied to carry out a specific function or a number of specific functions in accordance with the above-described method. The functional modules can be hardware modules or software modules. In other words, to the extent that it relates to the data processing unit, the invention can be implemented in the form of computer hardware or in the form of computer software or in a combination of hardware and software. To the extent that the invention is realized in the form of software, i.e. as a computer program product, all described functions are implemented by computer program instructions when the computer program is executed on a computer with a processor. The computer program instructions are implemented in this case in a manner known per se in any programming language and can be provided on the computer in any form, for example in the form of data packets that are transmitted over a computer network, or in the form of a computer program product stored on a disk, a CD-ROM or any other data medium.

The above-described properties, features and advantages of this invention and the manner in which they are achieved will become clearer and more easily understandable in conjunction with the following description of exemplary embodiments, which are explained in more detail in conjunction with the drawings. In detail:

DESCRIPTION OF THE INVENTION

Figure 1:
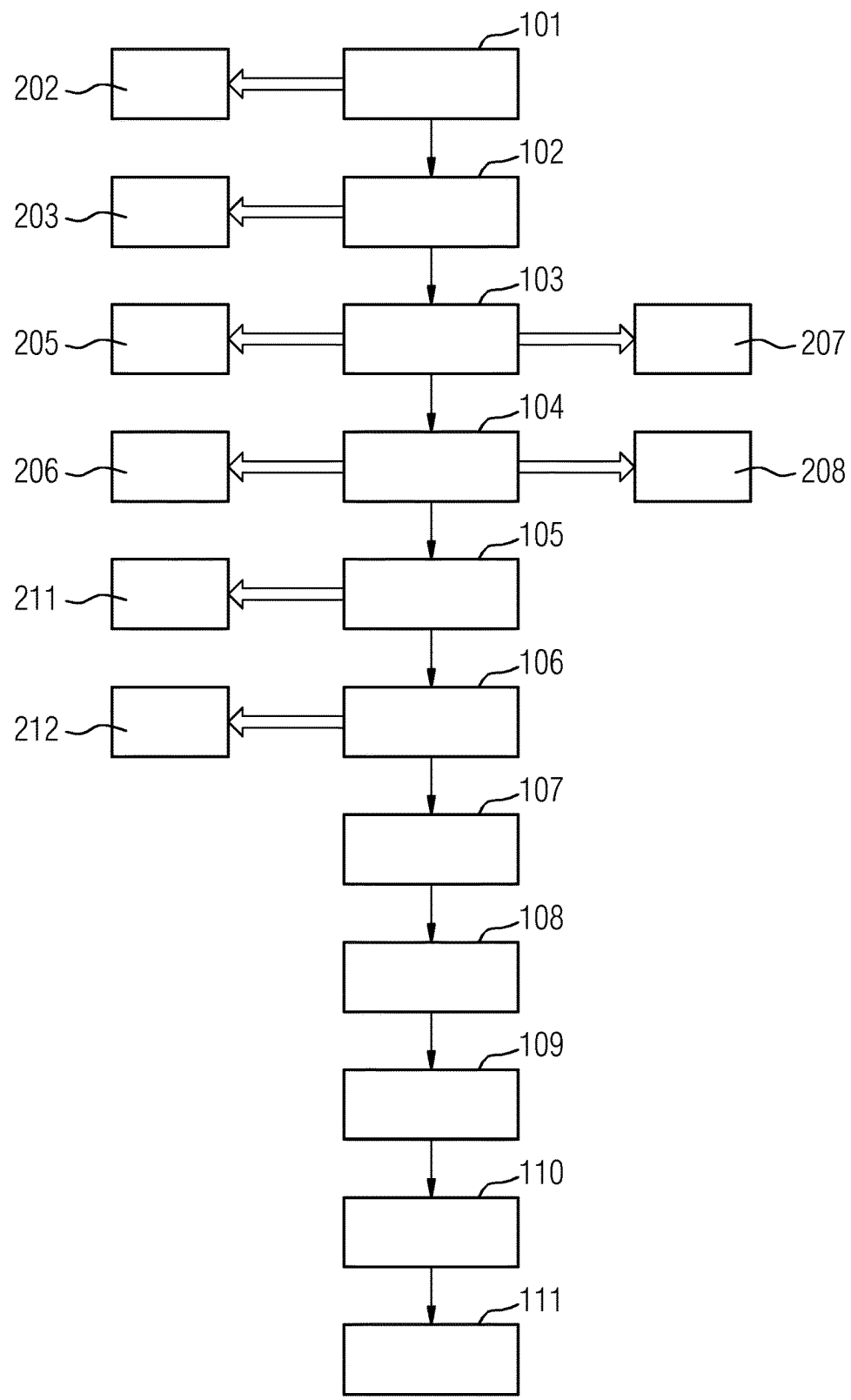
FIG. 1 shows the progress of a method according to the invention for determining selected points or regions.
Figure 2:
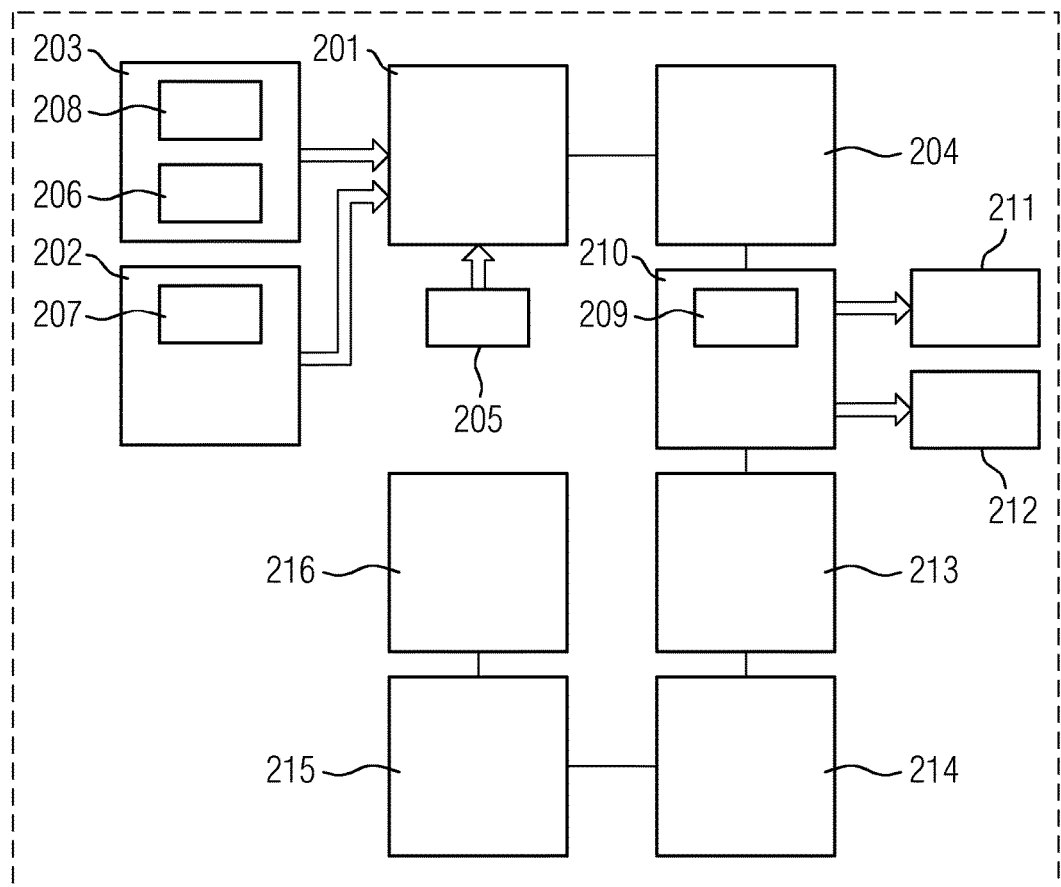
FIG. 2 shows a device according to the invention for determining selected points or regions.
Figure 3:
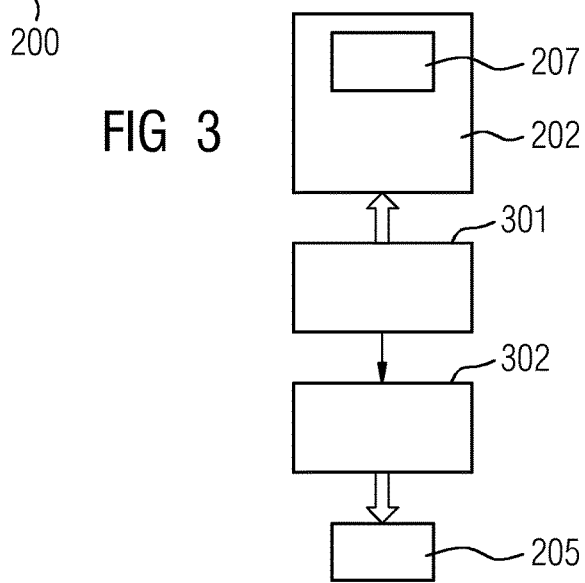
FIG. 3 shows the progress of a method according to the invention for ultrasound recording.
Figure 4:
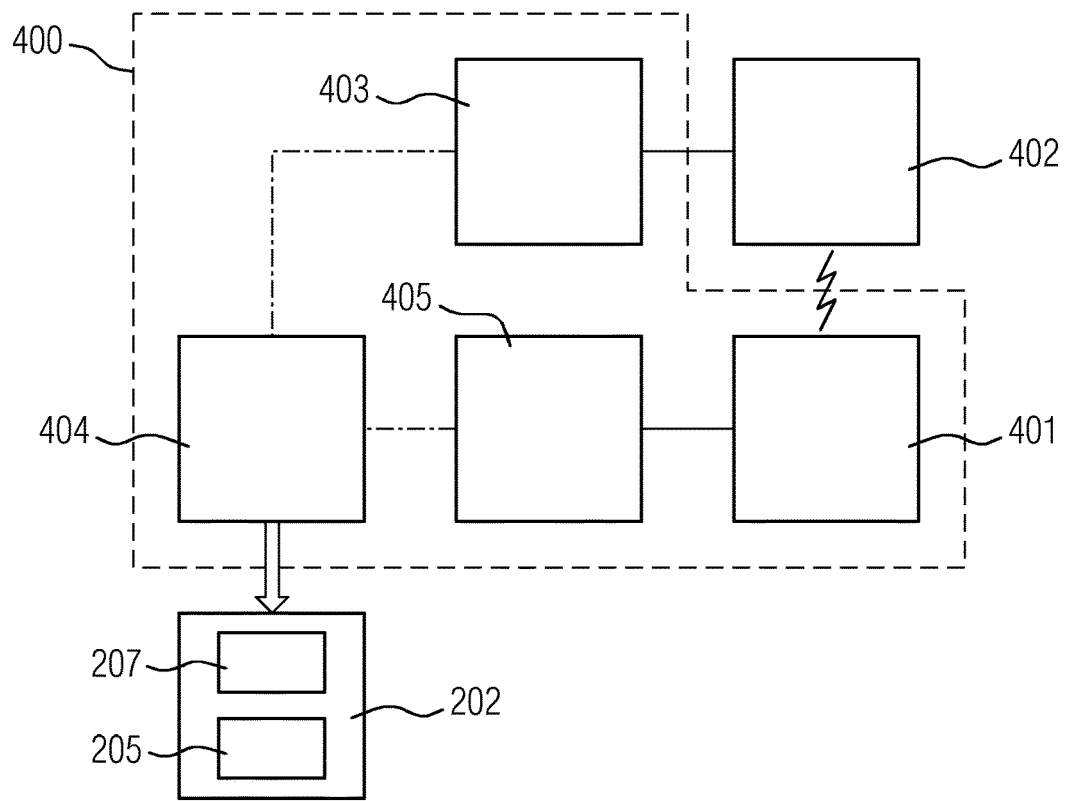
FIG. 4 shows a device according to the invention for ultrasound recording.
Figure 5:
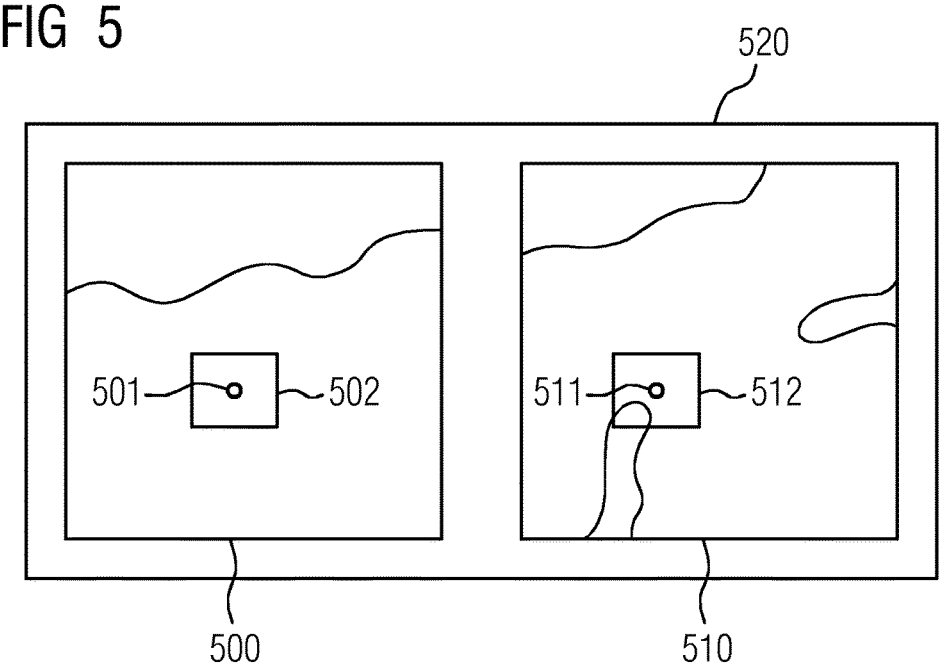
FIG. 5 shows illustrations of the corresponding points or regions in different deformation models.

All figures show the invention merely schematically and with the essential constituents thereof. Here, the same reference signs correspond to elements with the same or a comparable function.

A method, implemented by an appropriate device 200, for determining selected points and/or regions in medical recordings of a human breast 402 that is deformed in different ways is described on the basis of an example, in which a first recording of the breast 402 is carried out in the form of an ultrasound recording and a second recording of the breast 402 is carried out in the form of an x-ray recording. Here, the ultrasound recording is implemented with the aid of an automated three-dimensional breast ultrasound system comprising an ultrasound head 401, and the x-ray recording is implemented with the aid of an x-ray mammography system. Here, the breast 402 is deformed in a first way during the ultrasound recording and deformed in a different way during the x-ray recording.

In a first step 101 of the method according to the invention, the recording data record 202 of the ultrasound recording is obtained by means of an obtaining apparatus 201. In a further step 102, the recording data record 203 of the x-ray recording is obtained by means of the obtaining apparatus 201. To this end, the recording data records 202 are made available to the obtaining apparatus 201. The recording data record 201 of the ultrasound recording was obtained in advance by a method, carried out with the aid of an ultrasound recording device 400, for ultrasound recording of a human breast 402, in which the recording data record 202 is recorded with the aid of an ultrasound head 401 in a step 301 and information about the position of the breast 402 and/or the position of the ultrasound head 401 is acquired during the recording in a step 302 by way of suitable sensors.

Here, the acquisition 302 of information about the position of the breast 402 comprises an acquisition with the aid of a movement sensor 403, preferably a simple gyro sensor, of the tilt or twist of the breast 402 during the recording 301 relative to an initial location. To this end, the sensor 403 is attached to the rib cage 402 of the patient, in particular to the sternum or a different body region securely connected to the ribs; by way of example, it is adhesively bonded to the body.

The sensor 403 has a wireless contact with a base station 404 and it reports the rotations of the rib cage 402 of the patient to the base station 404. Before the ultrasound recording is started, the sensor 403 is calibrated to an initial location, with this advantageously being the supine position of the patient.

The use of a simple two-axis motion sensor is sufficient in this case for measuring the position of the rib cage of the patient or for determining the changes in the rib cage alignment between the various ultrasound measurements, since the cranial-caudal patient axis always remains the same under the condition that the patient lies on an examination couch and the feet always point to the same end of the examination couch. It is optionally possible to detect all three angle axes, as result of which the accuracy of the measurement can be slightly increased.

Since the case described here in an exemplary manner relates to an ultrasound head 401 guided on a defined trajectory in a defined movement direction, the movement of said ultrasound head is predetermined by a stepper motor during the recording and therefore known, the acquisition 302 of information about the position of the ultrasound head 401 merely comprises an acquisition of the movement of the ultrasound head 401 during the recording 301 with the aid of a single further two-axis motion sensor 405, co-moving with the ultrasound head 401, under the condition that, during the displacement of the ultrasound head 401, the sensor data are stored at at least two defined times. The position can then be calculated on the basis of the measurement data and the known spatial distance of the ultrasound head 401 between the two measurement points. The further sensor is likewise preferably a simple gyro sensor, which is attached at or on the ultrasound head 401.

In the case of a manually guided ultrasound system, in which no trajectories are predetermined, i.e. the ultrasound head 401 of which can be aligned freely in space, one or more movement sensors 405, with the aid of which the movement of the ultrasound head 401 can be recorded along all three spatial axes, are provided. Here, use is made, for example, of a number of sensors attached to the ultrasound head 401 and/or to a stationary support or any other suitable reference system, which sensors are able to acquire both a tilt or rotation of the ultrasound head 401 and a translational movement of the ultrasound head 401 during the recording, for example a centrifugal-force sensor and a distance sensor.

In both cases, the object of the sensors 405 attached to the ultrasound head 401 lies in acquiring the position of the ultrasound head 401 relative to the breast 402 and making this usable for the subsequent image registration. Instead of fastening the further sensor 405 directly to the ultrasound head 401, this sensor 405 can also be attached to a region of the ultrasound system, which is connected in a defined manner with the spatial alignment of the recorded ultrasound volume.

The position information of the breast 402 and the position information of the ultrasound head 401 provide recording parameters 205 characterizing the ultrasound recording, which recording parameters can be used for subsequent further processing of the data in addition to the actual image information 207.

Additionally, further sensors can be used for increasing the accuracy of the position acquisition, for example sensors for measuring the distance between the sensors 403, 405, attached to the rib cage 402 and the ultrasound head 401, during the recording 301 or sensors which establish the distance between these sensors 403, 405 and a spaced apart fixed point, for example the base station 404, during the recording 301.

If a plurality of ultrasound recordings are carried out, the recording data record 201 of the ultrasound recording preferably then comprises the data of all these ultrasound recordings. By way of example, three to five individual measurements of the breast 402 are established. The volumes recorded within the scope of these individual measurements generally overlap in the region of the nipple, but are rotated relative to one another about an angle because the patient is reoriented between the individual measurements in each case. Then, there is a correlation between the three to five volumes with the aid of the position information, that is to say information about the position of the rib cage 402 and/or the ultrasound head 401 during the recording 301. This means that the individual volumes are superposed or aligned in respect of one another by way of the base station 404. Therefore, image information 207 and recording parameters 205 are available for all individual recordings after the ultrasound recording.

In a further step 103 of the method according to the invention, these recording parameters 205 and the image information 207 of the ultrasound recording are acquired with the aid of an acquisition apparatus 204. In a further step 104, recording parameters 206 and image information 208 of the x-ray recording are acquired with the aid of the acquisition apparatus 204.

As already described above, the recording parameters 205 of the ultrasound recording are at least one item of information about the position of the breast 402 and/or the ultrasound head 401 during the recording 301. The recording parameters 206 of the x-ray recording are, in particular, DICOM data relating to recording angle, plate distances and compression forces. These recording parameters 205, 206 are either contained in the recording data records 202, 203 themselves or are made available separately.

The image information 208 from the x-ray recording and the image information 207 from the ultrasound recording relate, in particular, to individual features and/or areas, as are determinable by means of the acquisition apparatus 204 in a preferably automatic manner, for example by way of segmentation, such as the breast contour, the location of the nipple, which can be used as fixed point in the imaging, or the pectoral muscle. Suitable image information 207, 208 is provided with landmarks by the acquisition apparatus 204 for the purposes of subsequent use during the registration of the recording data records 202, 203 with the deformation models.

In a further step 105, a first deformation model 211 of the breast 402, which was deformed during the ultrasound recording, is produced with the aid of a production apparatus 209 on the basis of an initial model 210 of a non-deformed breast 402 using the recording parameters 205 and/or image information 207 of the ultrasound recording.

In a further step 106, a second deformation model 212 of the breast 402, which was deformed differently during the x-ray recording, is produced with the aid of the production apparatus 209 on the basis of the same initial model 210 using the recording parameters 206 and/or image information 208 of the x-ray recording.

There is no need to record the breast 402 in the non-deformed, i.e. substantially gravity-free state in the two steps 105, 106 mentioned last. Instead, suitable deformed models are produced by the production apparatus 209 in a case-specific manner, proceeding from a non-deformed initial model. This is carried out by simulating or calculating the compression and hence the deformation of the breast 402 during the respective recording or by resorting to compressions already calculated previously. In the process, there is a case-specific adaptation of the breast models 211, 212 to the real recording data record 202, 203.

The initial model 210 is a standardized, in particular generic breast model or an initial model selected from a number of stored initial models on the basis of specific, in particular patient-specific selection criteria. Here, the initial model 201 can also be based on a real measurement. Typically, the same initial model 210 is used for both deformation models 211, 212. However, it is also possible to use different initial models if the relationship between the employed initial models is set in such a way that a reciprocal unique coordinate transform is possible.

Once deformation models 211, 212 are produced, they can be stored in a model catalog, from where they can be selected again as a suitable model and used by the production apparatus 209 if defined conditions are present.

The recording parameters that are used for producing the deformation model 211 for the ultrasound recording are, in particular, the parameters already described above, such as tilt angle of the rib cage 402 and position of the ultrasound head 401 relative to the rib cage 402. The recording parameters that are used for producing the deformation model 212 for the x-ray recording are, in particular, recording angle, plate distances and compression forces. The image information 207, 208 already listed above is used both for producing the deformation model 211 for the ultrasound recording and for producing the deformation model 212 for the x-ray recording.

In a further step 107, there is a registration of the ultrasound deformation model 211 to the representation of the breast 402 in the ultrasound recording data record 202 with the aid of a registration apparatus 213. In a further step 208, there is a registration of the x-ray deformation model 212 to the representation of the breast in the x-ray recording data record 203 with the aid of the registration apparatus 213. These registrations 107, 108 correspond to the conventional manner of image registrations, as are known to a person skilled in the art. Therefore, there is no need to discuss this in any more detail here. Using the recording parameters 205, 206 and/or image information 207, 208 for the purposes of this registration may be advantageous.

Once these preparation steps have been completed, the practical application of the invention can be implemented within the scope of the work of the radiologist. To this end, a point 501 and/or region 502 from the ultrasound representation 500 of the breast 402 are selected in the ultrasound deformation model 211 with the aid of a selection apparatus 214 in a further step 109. Here, the selection can be implemented either manually, for example by the radiologist, or else automatically, for example on the basis of an automatic pattern recognition of medically relevant points 501 or regions 502. By way of example, the selection apparatus 214 can be a mouse pointer, which marks a point 501 or a region 502 in a representation 500 of the ultrasound image data.

In a subsequent step 110, there is automatic determination of a point 511 and/or region 512, corresponding to the selected point 501 and/or region 502, in the other representation 510 of the breast 402 in the x-ray deformation model 212 by way of a coordinate correlation using the initial model 210 of the non-deformed breast 402 with the aid of a determination apparatus 215. Since the non-deformed breast model 210 is the initial point for all deformation simulations or calculations underlying the deformed breast models 211, 212, the coordinate system of the non-deformed breast model 210 can be used here to establish a very exact coordinate correlation between the deformed breast models 211, 212.

In a concluding step 111, the point 501 and/or region 502 selected in the ultrasound recording is displayed using a display apparatus 216 in the representation 510 of the x-ray recording of the breast as point 511 and/or region 512, for example on adjacent monitors or in adjacent windows of a monitor 520.

The described method can also be carried out in another way by virtue of a point 511 or region 512 being selected in the x-ray representation 510 with the aid of the selection apparatus 214, which point or region is subsequently displayed in the ultrasound representation 500 as point 501 or region 502 with the aid of the display apparatus 216 after it was previously determined in an automatic manner with the aid of the determination apparatus 215.

The device 200 for carrying out the method according to the invention comprises a data processing unit, wherein, in particular, the obtaining apparatus 201, the acquisition apparatus 204, the production apparatus 209, the registration apparatus 213, the selection apparatus 214, the determination apparatus 215 and the display apparatus 216 are configured as functional modules of this data processing unit.

The invention proceeds from the concept of relating points 501, 511 and/or regions 502, 512 in images, obtained by imaging methods, of differently deformed objects (e.g. the human breast 402 in mammography and 3D ultrasound) to one another. While a multiplicity of recording parameters 206 are often known in x-ray and other imaging methods, which can be used for such an automated image registration, precise recording parameters, in particular in relation to the position of the breast 402, are usually not available in the case of ultrasound. The core concept of the invention lies in also registering the position (tilt) of the rib cage 402 and of the ultrasound head 401 during a breast ultrasound. Using the position of the ultrasound head 401 relative to the rib cage 402, which is then known in a case-specific manner, a plurality of ultrasound recordings can be linked to one another or a comparatively exact or automatic image registration with other modalities can be carried out.

Although the invention has been more specifically illustrated and described in detail by means of the preferred exemplary embodiment, nevertheless the invention is not restricted by the examples disclosed and other variations can be derived therefrom by the person skilled in the art, without departing from the scope of protection of the invention.

LIST OF REFERENCE SIGNS

101 Obtaining the ultrasound recording
102 Obtaining the x-ray recording
103 Acquiring the recording parameters of the ultrasound recording
104 Acquiring the recording parameters of the x-ray recording
105 Producing the ultrasound deformation model
106 Producing the x-ray deformation model
107 Registering the ultrasound deformation model
108 Registering the x-ray deformation model
109 Selecting a point
110 Determining a corresponding point
111 Displaying the corresponding point
200 Determination device
201 Obtaining apparatus
202 Ultrasound recording data record 203 X-ray recording data record
204 Acquisition apparatus
205 Ultrasound recording parameter
206 X-ray recording parameter
207 Ultrasound image information
208 X-ray image information
209 Production apparatus
210 Initial model
211 Ultrasound deformation model
212 X-ray deformation model
213 Registration apparatus
214 Selection apparatus
215 Determination apparatuses
216 Display apparatus
301 Recording step
302 Acquisition step
401 Ultrasound head
402 Breast, rib cage
403 Movement sensor on the rib cage
404 Base station
405 Movement sensor on the ultrasound head
500 Ultrasound representation
501 Point in the ultrasound representation
502 region in the ultrasound representation
510 X-ray representation
511 Point in the ultrasound representation
512 Region in the ultrasound representation
520 Monitor

The invention claimed is:

1. A method for determining selected points and/or regions in medical recordings of an object deformed in various ways, the method comprising the following steps:
   performing
   recording a recording data record of the deformed object with an ultrasound recording instrument;
   during the recording step, acquiring information about a position of the object and/or of the ultrasound recording instrument by way of at least one sensor for obtaining a first recording data record;
   acquiring recording parameters of, and/or image information from, the first recording, the recording parameters including at least one item of information about a position of the object and/or of the ultrasound recording instrument during the recording;
   producing a first deformation model of the deformed object on the basis of an initial model of a non-deformed object using the recording parameters and/or image information of the first recording or selecting a first deformation model from a model catalog using the recording parameters and/or image information of the first recording;
   registering the first recording data record with the first deformation model;
   obtaining a second recording data record of the object, but differently deformed, recorded by way of a different imaging method;
   acquiring recording parameters and/or image information of the second recording;
   producing a second deformation model of the deformed object on the basis of an initial model of a non-deformed object using the recording parameters and/or image information of the second recording or selecting a second deformation model from a model catalog using the recording parameters and/or image information of the second recording;
   registering the second recording data record with the second deformation model;
   selecting at least one of a point or region in the first deformation model of the object;
   automatically determining at least one of a point or region in the second deformation model of the object, which corresponds to the selected point and/or region, by coordinate correlation using the initial model of the non-deformed object; and
   displaying the determined point and/or region in the second deformation model of the object.

2. The method according to claim 1, wherein the object is a human breast, and the different imaging method is selected from the group consisting of x-ray mammography, tomosynthesis, and magnetic resonance imaging.

3. The method according to claim 1, wherein the deformed object is a human breast.

4. The method according to claim 1, wherein the acquiring step comprises acquiring one or both of a location or an orientation of the object during the recording.

5. The method according to claim 4, wherein the acquiring step comprises acquiring a tilt of the object relative to an initial location.

6. The method according to claim 1, wherein the step of acquiring information about the position of the ultrasound recording instrument comprises an acquisition of location and/or orientation of the ultrasound recording instrument during the recording.

7. The method according to claim 6, wherein the acquisition of location and/or orientation of the ultrasound recording instrument during the recording comprises acquiring a tilt of the ultrasound recording instrument relative to an initial location, and/or acquiring a movement of the ultrasound recording instrument.

8. The method according to claim 1, wherein the deformed object is a human breast and the process is an automated breast volume ultrasound.

9. The method according to claim 1, which comprises aligning a plurality of ultrasound recordings with respect to one another with the aid of the information about the position of the object and/or of the ultrasound recording instrument.

10. A computer program, comprising computer program instructions stored in non-transitory form for executing the steps of a method according to claim 1 when the computer program is executed on a computer.

11. A device for determining selected points and/or regions in medical recordings of an object deformed in various ways, the device comprising:
   an obtaining apparatus for obtaining a first recording data record, recorded by a method including the following steps:
      recording a recording data record of a deformed object with an ultrasound recording instrument;
      during the recording step, acquiring information about a position of the object and/or of the ultrasound recording instrument by way of at least one sensor;
   an acquisition apparatus for acquiring recording parameters of, and/or image information from, the first recording, wherein the recording parameters include at least one item of information about a position of at least one of the object or the ultrasound recording instrument during the recording;
   a production apparatus for producing a first deformation model of the deformed object on the basis of an initial model of a non-deformed object using the recording parameters and/or image information of the first recording or selecting a first deformation model from a model catalog using the recording parameters and/or image information of the first recording;
a registration apparatus for registering the first recording data record with the first deformation model;
an obtaining apparatus for obtaining a second recording data record of the same, but differently deformed object, recorded by way of a different imaging method;
an acquisition apparatus for acquiring recording parameters and/or image information of the second recording;
a production apparatus for producing a second deformation model of the deformed object on the basis of an initial model of a non-deformed object using the recording parameters and/or image information of the second recording or selecting a second deformation model from a model catalog using the recording parameters and/or image information of the second recording;
a registration apparatus for registering the second recording data record with the second deformation model;
a selection apparatus for selecting a point and/or region in the first deformation model of the object;
a determination apparatus for automatically determining a point and/or region in the second deformation model of the object, which corresponds to the selected point and/or region, by coordinate correlation using the initial model of the non-deformed object; and
a display apparatus for displaying the determined point and/or region in the second deformation model of the object.

12. The device according to claim 11, wherein the object is a human breast, and the different imaging method is selected from the group consisting of x-ray mammography, tomosynthesis, and magnetic resonance imaging.

* * * * *